US009918771B2

(12) United States Patent
Regadas (10) Patent No.: US 9,918,771 B2
(45) Date of Patent: Mar. 20, 2018

(54) POLYP REMOVAL DEVICE AND METHOD OF USE

(71) Applicant: Covidien LP, Mansfield, MA (US)

(72) Inventor: F. Sergio P. Regadas, Fortaleza-Ceara (BR)

(73) Assignee: COVIDIEN LP, Mansfield, MA (US)

( * ) Notice: Subject to any disclaimer, the term of this patent is extended or adjusted under 35 U.S.C. 154(b) by 134 days.

(21) Appl. No.: 13/711,201

(22) Filed: Dec. 11, 2012

(65) Prior Publication Data

US 2013/0103041 A1   Apr. 25, 2013

Related U.S. Application Data

(63) Continuation of application No. 12/363,086, filed on Jan. 30, 2009, now Pat. No. 8,328,803.

(Continued)

(51) Int. Cl.
*A61B 18/00*   (2006.01)
*A61B 17/3205*   (2006.01)
(Continued)

(52) U.S. Cl.
CPC ........ *A61B 18/00* (2013.01); *A61B 17/32056* (2013.01); *A61B 18/14* (2013.01);
(Continued)

(58) Field of Classification Search
CPC ............ A61B 17/221; A61B 17/32056; A61B 2017/2212; A61B 2018/1407; A61B 17/26; A61B 2018/141; A61B 2018/144; A61B 18/1445; A61B 2018/00601; A61B 2018/0063; A61B 2018/126; A61B 2018/1412; A61B 17/32; A61B 18/14; A61B 18/18; A61B 18/20;
(Continued)

(56) References Cited

U.S. PATENT DOCUMENTS 749,689 A    1/1904   Houghton
1,952,617 A  3/1934   Wappler
(Continued)

FOREIGN PATENT DOCUMENTS

DE    2415263    10/1975
DE    2514501    10/1976
(Continued)

OTHER PUBLICATIONS

U.S. Appl. No. 12/176,679, filed Jul. 21, 2008.
(Continued)

*Primary Examiner* — Nathan R Price
*Assistant Examiner* — Weng Lee (57) ABSTRACT

A device and system for removing polyps is provided and includes a tubular member having proximal and distal ends, a snare portion operably extending from within the distal end of the tubular member, the snare portion including a cutting member for severing the sealed tissue. The polyp removal device may further include a handle portion operatively extending from within the proximal end of the tubular member. The handle portion may be configured for operable engagement by a user and the cutting member may extend between distal ends of the first and second electrodes.

21 Claims, 4 Drawing Sheets

Related U.S. Application Data (60) Provisional application No. 61/063,158, filed on Jan. 31, 2008.

(51) Int. Cl.
*A61B 18/14* (2006.01)
*A61B 17/24* (2006.01)
*A61B 17/221* (2006.01)
*A61B 17/32* (2006.01)
*A61B 18/18* (2006.01)
*A61B 18/20* (2006.01)

(52) U.S. Cl.
CPC .............. *A61B 17/221* (2013.01); *A61B 17/24* (2013.01); *A61B 17/32* (2013.01); *A61B 18/18* (2013.01); *A61B 18/20* (2013.01); *A61B 2018/00345* (2013.01); *A61B 2018/00404* (2013.01); *A61B 2018/00482* (2013.01); *A61B 2018/00571* (2013.01); *A61B 2018/00607* (2013.01); *A61B 2018/00619* (2013.01); *A61B 2018/141* (2013.01); *A61B 2018/1407* (2013.01)

(58) Field of Classification Search
CPC ........... A61B 2018/00345; A61B 2018/00404; A61B 2018/00482; A61B 2018/00619; A61B 2018/00607
USPC ....... 606/39, 47–52, 110, 111, 113, 127–128
See application file for complete search history.

(56) References Cited

U.S. PATENT DOCUMENTS

| | | | |
|---|---|---|---|
| 1,963,636 A | 6/1934 | Wappler | |
| 1,967,015 A | 7/1934 | Wappler | |
| 2,002,559 A | 5/1935 | Wappler | |
| 2,008,525 A | 7/1935 | Wappler | |
| 2,054,149 A | 9/1936 | Charles | |
| 2,442,966 A | 6/1948 | Wallace | |
| 2,532,043 A | 11/1950 | Wallace | |
| 3,149,633 A | 9/1964 | Zingale | |
| 3,752,159 A | 8/1973 | Wappler | |
| 3,856,015 A | 12/1974 | Iglesias | |
| 4,011,872 A | 3/1977 | Komiya | |
| 4,024,869 A | 5/1977 | Bonnet | |
| 4,060,087 A | 11/1977 | Hiltebrandt et al. | |
| 4,068,667 A | 1/1978 | Iglesias | |
| 4,116,198 A | 9/1978 | Roos | |
| 4,134,406 A | 1/1979 | Iglesias | |
| 4,202,338 A | 5/1980 | Bitrolf | |
| 4,294,254 A | 10/1981 | Chamness | |
| 4,311,143 A | 1/1982 | Komiya | |
| 4,493,320 A * | 1/1985 | Treat ...................... | A61B 18/14 606/47 |
| 4,503,855 A | 3/1985 | Maslanka | |
| 4,718,419 A | 1/1988 | Okada | |
| 4,905,691 A | 3/1990 | Rydell | |
| 5,026,371 A | 6/1991 | Rydell et al. | |
| 5,066,295 A | 11/1991 | Kozak et al. | |
| 5,078,716 A * | 1/1992 | Doll ........................ | A61B 18/14 606/47 |
| 5,192,280 A | 3/1993 | Parins | |
| 5,197,964 A | 3/1993 | Parins | |
| 5,207,686 A | 5/1993 | Dolgin | |
| 5,290,284 A | 3/1994 | Adair | |
| 5,318,564 A | 6/1994 | Eggers | |
| 5,417,697 A | 5/1995 | Wilk et al. | |
| 5,460,629 A | 10/1995 | Shlain et al. | |
| 5,462,553 A | 10/1995 | Dolgin | |
| 5,817,093 A | 10/1998 | Williamson et al. | |
| 5,971,994 A | 10/1999 | Fritzsch | |
| 6,015,415 A | 1/2000 | Avellanet | |
| 6,050,995 A | 4/2000 | Durgin | |
| 6,071,283 A | 6/2000 | Nardella et al. | |
| 6,152,922 A | 11/2000 | Ouchi | |
| 6,235,026 B1 | 5/2001 | Smith | |
| 6,440,138 B1 * | 8/2002 | Reiley ................ | A61B 17/1671 606/45 |
| 6,517,539 B1 | 2/2003 | Smith et al. | |
| 6,730,097 B2 | 5/2004 | Dennis | |
| 6,743,228 B2 | 6/2004 | Lee et al. | |
| 6,773,432 B1 | 8/2004 | Clayman | |
| 6,827,717 B2 | 12/2004 | Brommersma et al. | |
| 6,852,108 B2 | 2/2005 | Barry | |
| 6,852,111 B1 | 2/2005 | Lieber | |
| 6,860,848 B2 | 3/2005 | Wosnitza et al. | |
| 6,942,017 B2 | 9/2005 | Gokan et al. | |
| 7,008,420 B2 | 3/2006 | Okada | |
| 7,037,307 B2 | 5/2006 | Dennis | |
| 7,104,990 B2 | 9/2006 | Jenkins et al. | |
| 2001/0009985 A1 | 7/2001 | Durgin et al. | |
| 2002/0072739 A1 | 6/2002 | Lee et al. | |
| 2002/0151889 A1 | 10/2002 | Swanson et al. | |
| 2002/0165540 A1 | 11/2002 | Bales et al. | |
| 2003/0009166 A1 | 1/2003 | Moutafis et al. | |
| 2003/0040744 A1 | 3/2003 | Latterell et al. | |
| 2003/0109870 A1 | 6/2003 | Lee et al. | |
| 2003/0114850 A1 | 6/2003 | McClurken et al. | |
| 2003/0125731 A1 | 7/2003 | Smith et al. | |
| 2003/0144661 A1 | 7/2003 | Brommersma et al. | |
| 2003/0153909 A1 | 8/2003 | Levinson | |
| 2003/0176859 A1 | 9/2003 | Levinson | |
| 2003/0181906 A1 | 9/2003 | Boebel et al. | |
| 2003/0204188 A1 | 10/2003 | Morrison et al. | |
| 2003/0212389 A1 | 11/2003 | Durgin et al. | |
| 2003/0216731 A1 | 11/2003 | Dennis | |
| 2004/0064139 A1 | 4/2004 | Yossepowitch | |
| 2004/0106920 A1 | 6/2004 | Jenkins et al. | |
| 2004/0153059 A1 | 8/2004 | Okada | |
| 2004/0199159 A1 | 8/2004 | Lee et al. | |
| 2004/0220564 A1 | 11/2004 | Ho et al. | |
| 2005/0070889 A1 | 3/2005 | Nobis et al. | |
| 2005/0085808 A1 | 3/2005 | Nakao | |
| 2005/0096650 A1 | 5/2005 | Ouchi | |
| 2005/0119652 A1 | 6/2005 | Vetter et al. | |
| 2005/0131402 A1 | 6/2005 | Ciarrocca et al. | |
| 2005/0131403 A1 | 6/2005 | Chang | |
| 2005/0137591 A1 | 6/2005 | Barry et al. | |
| 2005/0171531 A1 | 8/2005 | Eliachar et al. | |
| 2005/0171532 A1 | 8/2005 | Ciarrocca | |
| 2005/0209590 A1 | 8/2005 | Terakura | |
| 2005/0222568 A1 | 10/2005 | O'Sullivan | |
| 2005/0251134 A1 | 11/2005 | Woloszko | |
| 2005/0283150 A1 | 12/2005 | Moutafis et al. | |
| 2006/0009759 A1 | 1/2006 | Christian et al. | |
| 2006/0030846 A1 | 2/2006 | Buehlmann et al. | |
| 2006/0036234 A1 | 2/2006 | Durgin et al. | |
| 2006/0052774 A1 | 3/2006 | Garrison et al. | |
| 2006/0178670 A1 | 8/2006 | Woloszko et al. | |
| 2007/0198011 A1 | 8/2007 | Sugita | |
| 2007/0208339 A1 * | 9/2007 | Arts .................. | A61B 17/32056 606/47 |
| 2007/0250012 A1 * | 10/2007 | Lu ..................... | A61B 17/32056 604/168.01 |
| 2007/0270796 A2 * | 11/2007 | Girard .................... | A61B 18/14 606/45 |
| 2008/0221587 A1 | 9/2008 | Schwartz | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |

(56) References Cited

FOREIGN PATENT DOCUMENTS

| | | |
|---|---|---|
| DE | 10045375 | 10/2002 |
| DE | 19738457 | 1/2009 |
| EP | 0 467 501 A | 1/1992 |
| EP | 1159926 | 12/2001 |
| EP | 1 829 494 | 9/2007 |
| GB | 1 490 585 A | 11/1977 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-014922 | 1/1998 |
| JP | H10 14922 A | 1/1998 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 93/21845 A | 11/1993 |
| WO | WO 00/36986 | 6/2000 |
| WO | WO 01/54604 | 8/2001 |
| WO | WO 05/110264 | 11/2005 |

OTHER PUBLICATIONS

U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature: Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vesesl Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(56) References Cited

OTHER PUBLICATIONS

Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
International Search Report and Written Opinion of the International Searching Authority dated Jun. 16, 2009 issued by the (56) References Cited

OTHER PUBLICATIONS

European Patent Office in counterpart International Application No. PCT/US2009/032690 filed Jan. 30, 2009.
European Search Report dated Nov. 7, 2013.
Japanese Office Action from Japanese Patent Application No. 2013-146277 dated Feb. 2, 2015.
Canadian Office Action corresponding to Canadian Application No. 2,713,898 dated Oct. 26, 2015.

* cited by examiner

POLYP REMOVAL DEVICE AND METHOD OF USE

CROSS-REFERENCE TO RELATED APPLICATIONS

This application is a continuation application of U.S. patent application Ser. No. 12/363,086, filed Jan. 30, 2009, which claims the benefit of and priority to U.S. Provisional Patent Application Ser. No. 61/063,158, titled "Endoscopic Flexible Loop for Gastrointestinal Polypectomy and Mucosal Resection Using LigaSure™ Sealing Technology", by Wexner et al., filed Jan. 31, 2008, the entire contents of these applications are incorporated by reference herein.

BACKGROUND

Technical Field

The present disclosure relates to devices and methods for the removal of internal tissue and, more particularly, to snare-type devices including a pair of electrodes for treating tissue prior to excision.

Background of Related Art

A polyp is an abnormal growth of tissue projecting from a mucous membrane. A polyp that is attached to the surface of the mucous membrane by a narrow elongated stalk is said to be pedunculated. If no stalk is present, the polyp is said to be sessile. Polyps are commonly found in the colon, stomach, nose, urinary bladder and uterus. Polyps may also form elsewhere in the body where mucous membranes exist, for example, the cervix and small intestine.

The surgical procedure for removing a polyp is generally referred to as a "polypectomy". Polypectomys are generally endoscopic or laparoscopic procedures performed through the oral or anal cavities. When the location of the polyp permits, the polypectomy may be performed as an open procedure. Conventional polypectomys are completed using various apparatus and techniques known in the art.

As noted above, there are two forms of polyps, sessile and pedunculated. The stalkless or sessile polyps are generally removed using electrical forceps. For example, the excess tissue projecting from the mucous membrane is cauterized and torn from the tissue wall. Pedunculated polyps, or those with stalks, tend to be larger with a greater blood supply. The size and shape of pedunculated polyps typically do not lend themselves to being removed using traditional forceps. Unlike sessile polyps, polyps with a stalk cannot simply be grasped in the jaw members of an electrosurgical forceps and be torn from the tissue wall. Instead, the polypectomy is performed using a surgical snare device.

Conventional snare devices are configured with a snare for looping over the distal end of a hanging polyp and tightening securely around the stalk of the polyp. By constricting the snare, and selectively applying energy to the snare, the device may cauterize or seal the polyp at the stalk as the polyp is severed from the tissue wall. Conventional snare devices may be configured for monopolar or bipolar use. Excising a polyp using a conventional snare device typically involves cutting or otherwise separating the polyp from the tissue wall as the snare device is activated and constricted about the stalk of the polyp. In this manner, the polyp is cauterized as the snare passes through the tissue.

SUMMARY

Disclosed is a device configured for removing polyps. In one embodiment, the polyp removal device includes a tubular member having proximal and distal ends, a snare portion operably extending from within the distal end of the tubular member and including first and second electrodes configured to seal tissue therebetween, the snare portion further including a cutting member for severing the sealed tissue. The polyp removal device may further include a handle portion operatively extending from within the proximal end of the tubular member. The handle portion may be configured for operable engagement by a user. The cutting member may extend between distal ends of the first and second electrodes.

The polyp removal device may be configured to grasp the stalk of a polyp between the first and second electrodes. The first and second electrodes may be hingedly attached to the cutting member. The snare portion may be configured to be retracted within the tubular member. The snare portion may be retracted within the tubular member upon retraction of the handle portion relative to the base portion.

A system including the polyp removal device may further include an electrosurgical generator. The electrodes may be electrically connected to the electrosurgical generator. The distal end of the tubular member may include a spacer member for preventing the first and second electrodes from contacting one another. Alternatively, at least one of the first and second electrodes may include a spacer mounted thereon for preventing contact between the first and second electrodes.

Also provided is a polyp removal device including a tubular member having proximal and distal ends, a handle portion operatively extending from the proximal end of the tubular member, and a snare portion slidably supported within the lumen of the tubular member and operably extending from the distal end of the tubular member, the snare portion including first and second electrodes operably mounted thereto for sealing tissue therebetween, wherein at least one of the first and second electrodes includes at least one spacer mounted thereon for preventing contact between the first and second electrodes. The snare portion of the polyp removal device may be retractable with the tubular member.

Additionally provided is a method of removing a polyp. The method includes the steps of providing a polyp removal device including, a tubular member having proximal and distal ends, a snare portion slidably supported within the lumen of the tubular member and operably extending from the distal end of the tubular member, the snare portion including first and second electrodes operably mounted thereto for sealing tissue therebetween, wherein at least one of the first and second electrodes includes at least one spacer mounted thereon for preventing contact between the first and second electrodes, extending the snare portion relative to the tubular member, looping the snare portion about a portion of a polyp, retracting the snare portion relative to the tubular member to capture the portion of the polyp between the first and second electrodes, and activating the first and second electrodes.

The method may further include the steps of partially advancing the snare portion relative to the tubular member, retracting the tubular member and the snare portion relative to the polyp and severing the polyp from surrounding tissue.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF EMBODIMENTS

The foregoing summary, as well as the following detailed description will be better understood when read in conjunction with the appended figures. For the purpose of illustrating the present disclosure, various embodiments are shown. It is understood, however, that the present disclosure is not limited to the precise arrangement and instrumentalities shown.

As shown in the drawings and described throughout the following description, as is traditional when referring to relative positioning on an object, the term "proximal" refers to the end of the apparatus that is closer to the user and the term "distal" refers to the end of the apparatus that is further from the user.

Referring to FIGS. 1-4, an embodiment of the presently disclosed polyp removal device is shown therein and is generally designated as polyp removal device 100. Polyp removal device 100 includes an elongated tubular member 110, a handle portion 120 extending proximally from tubular member 110, and a snare portion or assembly 130 operably engaged with handle portion 120 and extending distally from within elongated tube 110. Polyp removal device 100 may be any suitable length and size for accessing various locations throughout the body. Device 100 may be configured for removal of suitable types of polyps of any size, or may be configured for general mucosal resection or removal of any suitable tissue mass. Preferably, polyp removal device 100 is configured for endoscopic, laparoscopic or transluminal insertion.

Figure 1:
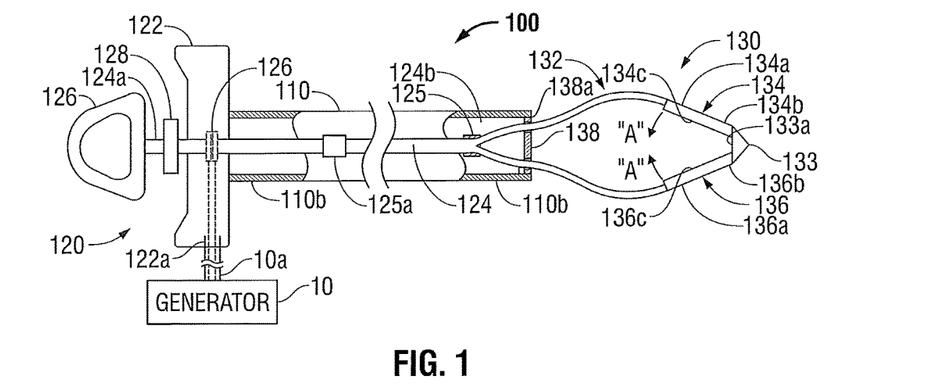
FIG. 1 is a partial cross-sectional, top plan view of a polyp removal device according to an embodiment of the present disclosure, shown in a first or extended position.
Figure 2:
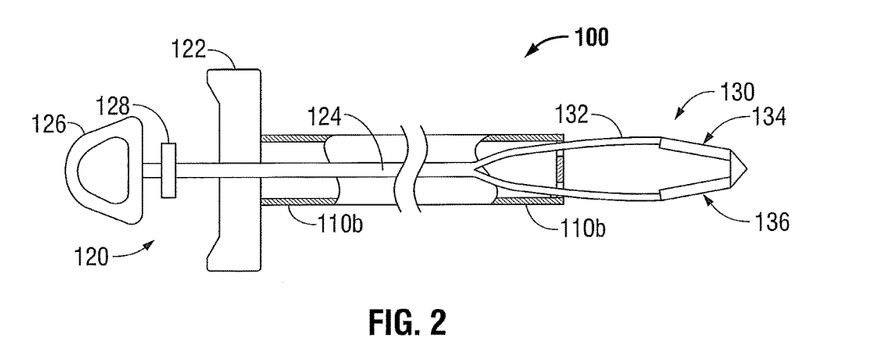
FIG. 2 is a partial cross-sectional top plan view of the polyp removal device of FIG. 1, shown in a partially retracted position.
Figure 3:
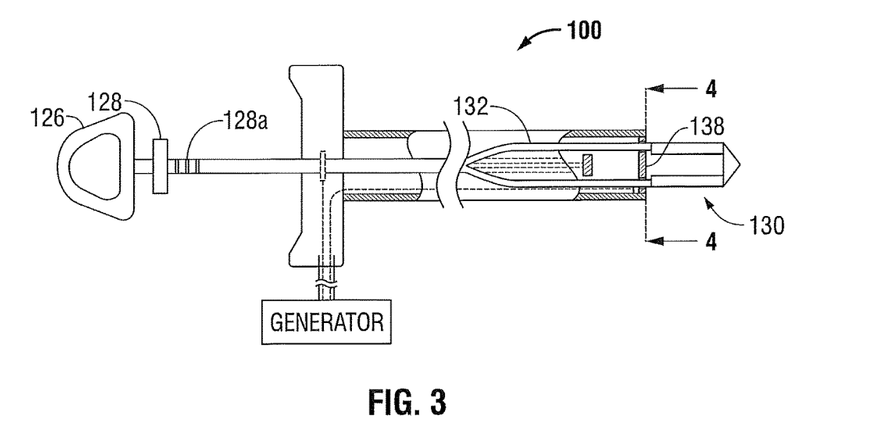
FIG. 3 is a partial cross-sectional top plan view of the polyp removal device of FIG. 1, shown in a retracted position.
Figure 4:
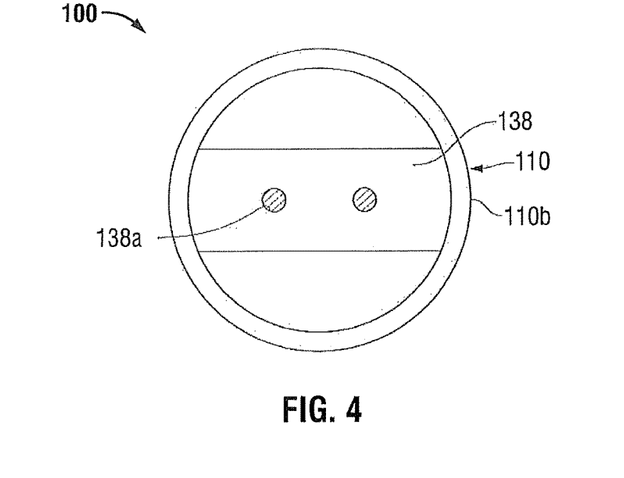
FIG. 4 is a cross-section end view of the polyp removal device of FIGS. 1-3 taken along line 4-4 of FIG. 3.

Referring initially to FIGS. 1-3, elongated tubular member 110 includes proximal and distal ends 110a, 110b. Proximal end 110a of tubular member 110 is operably coupled to handle portion 120. As will be described in further detail below, handle portion 120 may be integrally formed with tubular member 110. Alternatively, handle portion 120 may be releasably secured to tubular member 110, or may instead be securely affixed to tubular member 110. Tubular member 110 may be flexible, semi-rigid, or rigid and may be constructed of metal, alloy, plastic, polymers, or any other suitable material. Distal end 110b of tubular member 110 is configured to slidingly receive a proximal end of snare portion 130.

Although the following description of the polyp removal device 100 will be described in the form of a snare-type device, the aspects of the present disclosure may be modified for used with alternative handle configurations, including a pistol grip style device, mechanically and/or remotely actuated handles, other suitable types of devices or handle arrangements. As one example, polyp removal device 100 may be incorporated as a pistol grip style laparoscopic device like some of the LigaSure™ tissue fusion devices sold by Valleylab of Boulder, Colo.

Still referring to FIGS. 1-3, handle portion 120 of polyp removal device 100 includes a base 122 coupled to proximal end 110a of tubular member 110, a connector shaft 124 extending through base 122, and a handle 126 operably coupled to a proximal end 124a of connector shaft 124. In one embodiment, base 122 of handle portion 120 may be securely affixed to proximal end 110a of tubular member 110 using adhesive, bonding, mechanical fasteners, welding or other suitable methods. Alternatively, base 122 may be releasably connected to tubular member 110 using mechanical fasteners, threaded engagement, friction fitting, bayonet connections, or the like. In this manner, snare portion 130 may be removed and replaced through proximal end 110a of tubular member 110. Base 122 of handle portion 120 may instead be integrally formed with proximal end 110a of tubular member 110. Handle 126 is configured for operable engagement by a user. Handle 126 may be knurled or may include a coating for facilitating engagement by a user.

Base 122 of handle portion 120 is further configured for operable engagement with a generator 10. Base 122 defines a connection port 122a for receiving an electrical cord 10a extending from generator 10. Electrical cord 10a extends from connection port 122a through base 122 and is operably coupled to first and second electrodes 134, 136 of snare portion 130. Electrical cord 10a may be directly coupled to first and second electrodes 134, 136. Alternatively, electrical cord 10a may couple with a coupling member 123 mounted to shaft 124. In this manner, coupling member 123 electrically couples generator 10 with first and second electrodes 134, 136 along shaft 124. Generator 10 may include any suitable generator configured to selectively provide energy to electrodes 134, 136. For example, radiofrequency energy, either monopolar or bipolar may be provided to electrodes 134, 136. In other embodiments, ultrasonic, microwave, or laser energy may be provided. Depending on the energy modality utilized, snare 130 and/or electrodes 134, 136 may have to be reconfigured in order the handle the different types of energy.

In an embodiment where radiofrequency energy is utilized, to increase safety, bipolar radiofrequency energy is preferred because the energy will travel between first and second electrodes 134, 136 instead of between the snare 130 and some remote return pad. In one particular embodiment, generator 10 takes the form of a battery-powered generator that is integral with, or releasably coupled to, polyp removal device 100. In this example, electrical cord 10a is not needed. Generator 10 may also be configured to monitor the electrical properties of the tissue maintained between first and second electrodes 134, 136 and signal to the clinician when conditions have been met that are suitable for sealing of tissue.

Still referring to FIGS. 1-3, connector shaft 124 includes an elongated tubular shaft including proximal and distal ends 124a, 124b. Proximal end 124a is configured for operable engagement with handle 126. Handle 126 may be securely affixed, releasable coupled, or integrally formed with proximal end 124a of connector shaft 124. Handle portion 120 may further include a stop member 128 positioned about connector shaft 124 between base 122 and handle 126. Stop member 128 prevents complete retraction of connector shaft 124 past base 122. Proximal end 124a may be configured to securely retain stop member 128, or instead, may include grooves or indents 128a for selectively positioning stop member 128 thereabout. In this manner, adjustment of stop member 128 reduces or increases the amount of extension of snare portion 130. Alternatively, stop member 128 may be configured to selectively engage distal end 124a of connector shaft 124 through the incorporation of a mechanical fastener or the like (not shown). Distal end 124b of connector shaft 124 is operably coupled to snare portion 130. Distal end 124b may be permanently coupled, releasably coupled or integrally formed with snare portion 130.

Snare portion 130 includes a snare 132 formed of a loop of rigid or semi-rigid wire or flexible band. Snare 132 may be constructed of metal, polymer or other suitable material. In the illustrated embodiment, snare 132 is non-conductive; however, snare 132 may be conductive or partially conductive. Coupled to snare 132 in any suitable manner near a distal end 130b of snare portion 130 are first and second electrodes 134, 136. As discussed above, first and second electrodes 134, 136 are electrically coupled to generator 10 to receive electrosurgical energy therefrom. First and second electrodes 134, 136, which may be of any suitable construction, each include at least a tissue contacting surface 134c, 136c. In some embodiments, first and second electrodes 134, 136 are each formed from a tissue contacting surface 134c, 136c and an insulative body portion. Tissue contacting surfaces 134c, 136c may include any configuration suitable for treating tissue, including hatching, grooves and detents (not shown). In one embodiment, generator 10, first and second electrodes 134, 136, and tissue contacting surfaces 134c, 136c, are all configured for sealing tissue.

Positioned between first and second electrodes 134, 136 is a connection member 133. Distal ends 134b, 136b of first and second electrodes 134, 136, respectively, are coupled to connection member 133. First and second electrodes 134, 136 and connection member 133 are configured such that in a first or extended position, proximal ends 134a, 136a of first and second electrodes 134, 136, respectively, are substantially spaced from one another. As will be discussed in further detail below, this configuration opens snare 132 to facilitate the looping of snare 132 over a polyp "P" (FIG. 6) and the positioning of first and second electrodes 134, 136 about stalk "S" of polyp "P".

First and second electrodes 134, 136 and connection member 133 are further configured such that as proximal end 130a of snare portion 130 is retracted within distal end 110b of tubular member 110, proximal ends 134a, 136a of first and second electrodes 134, 136, respectively, are approximated towards each other, in the direction of arrows "A" (FIG. 1). In this manner, first and second electrodes 134, 136 and connection member 133 act like a jaw assembly, thereby compressing stalk "S" of polyp "P" between first and second electrodes 134, 136. To prevent first and second electrodes 134, 136 from contacting one another, distal end 110b of tubular member 110 may include a spacer member 138 through which snare 132 may extend. Spacer member 138 spans distal end 110b of tubular member 110 and includes a pair of apertures 138a through which snare 132 is received. Apertures 138a are spaced such that upon retraction of proximal end 130a of snare portion 130 within tubular member 110, proximal end 134a, 136a of first and second electrodes 134, 136 are approximated towards one another. Apertures 138a are further configured to prevent first and second electrodes 134, 136 contacting one another. Release of proximal end 130a of snare portion 130 from within distal end 110b of tubular member 100 permits proximal ends 134a, 136a of first and second electrodes 134, 136 to approximate away from one another and eventual return to their initial position.

In an alternative embodiment, one or both of first and second electrodes 134, 136 may include one or more spacers 134d, 136d (FIG. 5) formed on respective proximal ends 134a, 136a. Spacers 134d, 136d are configured to prevent contact between first and second electrodes 134, 136.

Figure 6:
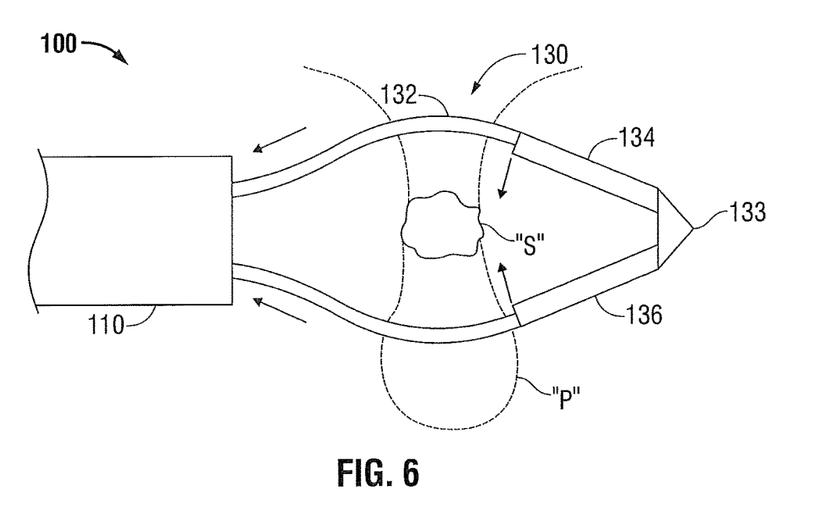
FIG. 6 is a partial top plan view of the distal end of the polyp removal device of FIGS. 1-4, in a first or extending position about a polyp.
Figure 7:
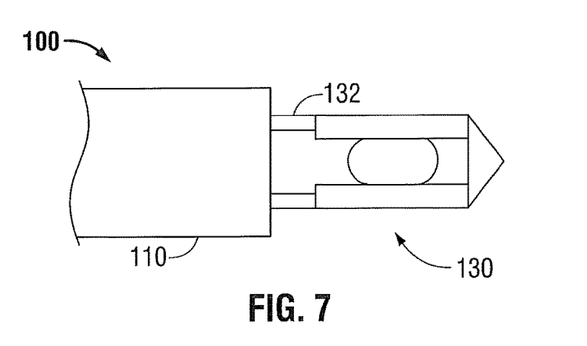
FIG. 7 is a partial top plan view of the distal end of the polyp removal device of FIG. 6, in a retracted position about a polyp.
Figure 8:
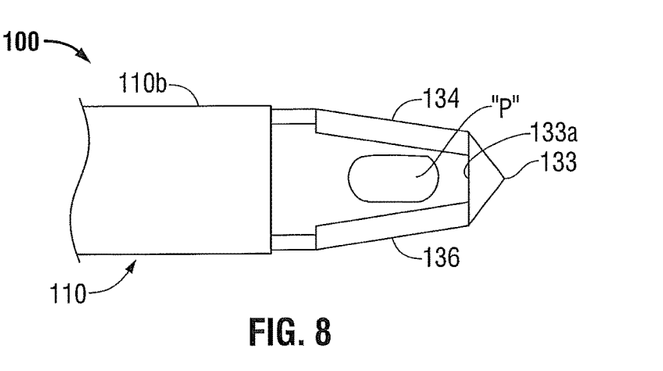
FIG. 8 is a partial top plan view of the distal end of the polyp removal device of FIGS. 6 and 7, in a partially advanced position about a polyp.

Connection member 133 extends between first and second electrodes 134, 136 and is configured to maintain distal ends 134b, 136b of first and second electrodes 134, 136, in a spaced relationship throughout the tissue excising procedure. As described above, in a first or extended position, proximal ends 134a, 136a of first and second electrodes 134, 136 are maintained in a substantially spaced apart relationship. This configuration facilitates positioning of snare 132, and first and second electrodes 134, 136 in particular, about stalk "S" of a polyp "P" (FIG. 6). Distal ends 134b, 136b of first and second electrodes 134, 136 are coupled to connection member 133 in a manner that permits pivoting, hinging, or flexing of first and second electrodes 134, 136 relative to connection member 133 as snare 132 is constricted about stalk "S" of polyp "P". First and second electrodes 134, 136 and/or connection member 133 may be formed of flexible material, or may instead include a hinge mechanism or any other suitable configuration capable of permitting first and second electrodes 134, 136 to pivot, hinge, or flex relative to connection member 133. In the event that proximal ends 134a, 136a of first and second electrodes 134, 136 are approximated away from one another by the configuration of connection member 133, snare 132 may provide the spring force to maintain proximal ends 134a, 136a substantially spaced apart when polyp removal device 100 is in a first or extended position.

Connection member 133 further includes at least a first sharpened surface 133a. First sharpened surface 133a is formed between distal ends 134b, 136b of first and second electrodes 134, 136 and may be configured to severe stalk "S" of polyp "P" after proper sealing of the tissue. In addition, or alternatively, the outer surface of connection member 133 may be sharpened to facilitate excising of polyp "P".

Referring now to FIGS. 1-3 and 6-8, one embodiment of the operation of polyp removal device 100 will be described. Initially, distal end 110b of tubular member 110 is inserted into a patient. As discussed above, introduction of polyp removal device 100 may be accomplished through an endoscopic or laparoscopic port, or may be inserted transluminally through the mouth or anus. To facilitate insertion of tubular member 110 into the body, in one embodiment (FIG. 5), snare portion 130a is completely retracted within tubular member 110.

Once distal end 110b of tubular member 110 is positioned near a polyp "P" to be removed, snare portion 130 is extended distally by advancing handle 126 of handle portion 120 relative to base 122. The spring-like configuration between first and second electrodes 134, 136 and connection member 133 results in proximal ends 134a, 136a of first and second electrodes 134, 136 approximating away from each other as handle 126 is advanced and proximal end 130a of snare portion 130 is released from tubular member 110. The separating of proximal ends 134a, 136a of first and second electrodes 134, 136 opens snare 132 and facilitates positioning of snare 132 about stalk "S" of polyp "P". Once snare 132 positioned such that stalk "S" is received between first and second electrodes 134, 136, handle 126 may be retracted or, in the alternative, tubular member 110 may be advanced to constrict snare 132 about stalk "S". As proximal end 130a of snare portion 130 is received within distal end 110b of tubular member 110 through spacer member 138, proximal ends 134a, 136a of first and second electrodes 134, 136 are approximated towards one another, thereby capturing stalk "S" of polyp "P" therebetween. Other methods of approximating first and second electrodes 134, 136 towards one another are contemplated by the present invention. For example, another instrument separate from polyp removal device 100 may be utilized.

Continued retraction of snare portion 130 within tubular member 110 causes first and second electrodes 134, 136 to compress stalk "S" of polyp "P". Once the clinician is satisfied stalk "S" is sufficiently received between first and second electrodes 134, 136, generator 10 may be activated to treat the tissue between first and second electrodes 134, 136. Alternatively, and as discussed above, generator 10 may include a system for monitoring the electrical properties of the tissue between first and second electrodes 134, 136. Once a predetermined condition has been satisfied, preferably, a condition suitable to promote tissue sealing, generator 10 signals to the clinician that the tissue is ready to be sealed, at which point, generator 10 may automatically provide electrosurgical energy to tissue contacting surfaces 134c, 136c, or the clinician may activate generator 10 to provide the energy to seal the tissue. Electrosurgical energy is provided to tissue contacting surfaces 134c, 136c until the tissue of stalk "S" is properly sealed. Electrosurgical energy may be provided at a range of frequencies, over a variable duration, and may be continuous or intermittent, depending of the type of tissue being treated and the thickness of the tissue. Furthermore, the monitoring function may include for a signal to denote that the sealing is finished and that severing of the polyp "P" may take place.

In some embodiments, in order to effectively seal larger vessels (or tissue) two predominant mechanical parameters should be accurately controlled—the pressure applied to the vessel (tissue) and the gap distance between the electrodes—both of which are affected by the thickness of the sealed vessel. More particularly, accurate application of pressure may be important to oppose the walls of the vessel; to reduce the tissue impedance to a low enough value that allows enough electrosurgical energy through the tissue; to overcome the forces of expansion during tissue heating; and to contribute to the end tissue thickness, which is an indication of a good seal. It has been determined that a typical fused vessel wall is preferably between 0.001 and 0.006 inches. Below this range, the seal may shred or tear and above this range the lumens may not be properly or effectively sealed.

With respect to smaller vessels, the pressure applied to the tissue tends to become less relevant, whereas the gap distance between the electrically conductive surfaces becomes more significant for effective sealing. In other words, the chances of the two electrically conductive surfaces touching during activation increases as vessels become smaller.

Figure 5:
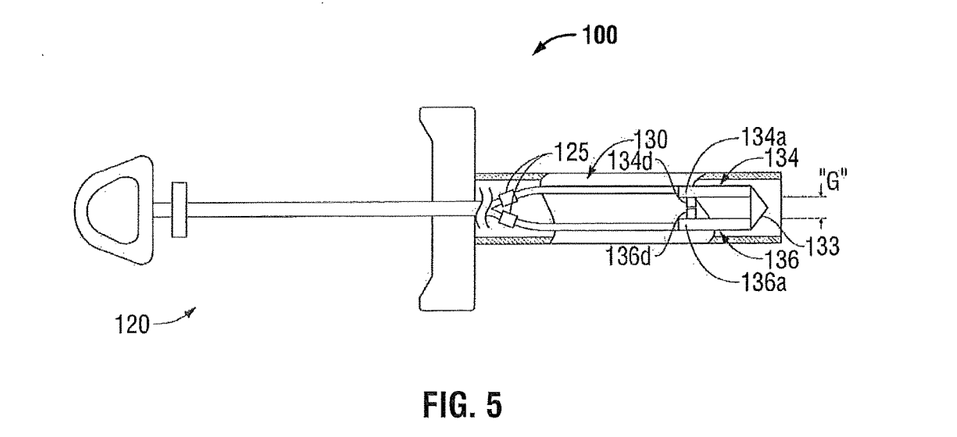
FIG. 5 is a partial cross-section top plan view of an alternative embodiment of a polyp removal device according to the present disclosure in a completely retracted position.

As mentioned above, at least one electrode, e.g., 134, may include a stop member 134d that limits the movement of the two opposing electrodes 134, 136 relative to one another. Stop member 134d may extend from the tissue contacting surface 134c a predetermined distance according to the specific material properties (e.g., compressive strength, thermal expansion, etc.) to yield a consistent and accurate gap distance "G" during sealing (FIG. 5). In one embodiment, the gap distance between opposing tissue contacting surfaces 134c, 136c during sealing ranges from about 0.001 inches to about 0.006 inches and, preferably, between about 0.002 and about 0.003 inches. The non-conductive stop members 134d, 136d may be molded onto electrodes 134, 136 (e.g., overmolding, injection molding, etc.), stamped onto electrodes 134, 136 or deposited (e.g., deposition) onto electrodes 134, 136. For example, one technique involves thermally spraying a ceramic material onto the surface of the electrodes 134, 136 to form the stop members 134d, 136d, respectively. Several thermal spraying techniques are contemplated that involve depositing a broad range of heat resistant and insulative materials on various surfaces to create stop members 134d, 136d for controlling the gap distance between electrically conductive surfaces 134c, 136c.

It has also been found that the pressure range for assuring a consistent and effective seal may be between about 3 kg/cm.sup.2 to about 16 kg/cm.sup.2 and, preferably, within a working range of 7 kg/cm.sup.2 to 13 kg/cm.sup.2. Manufacturing an instrument that is capable of providing a closure pressure within this working range has been shown, in some embodiments, to be effective for sealing arteries, tissues and other vascular bundles.

As can be appreciated, controlling the compressive force between with first and second electrodes 134, 136 as snare portion 130 is retracted may facilitate and assure consistent, uniform and accurate closure pressure about the tissue within the desired working pressure range of about 3 kg/cm.sup.2 to about 16 kg/cm.sup.2 and, preferably, about 7 kg/cm.sup.2 to about 13 kg/cm.sup.2. By controlling the intensity, frequency and duration of the electrosurgical energy applied to the tissue, the user can either cauterize, coagulate/desiccate, seal and/or simply reduce or slow bleeding.

In one embodiment, by controlling the force applied to handle 126, the resulting tension in snare portion 130 may be adjusted, which, in turn, regulates the overall pressure between electrodes 134, 136 to within the above-identified desired sealing range. A sensor 125 may be employed to accomplish this purpose and may be mechanically coupled to handle portion 120 and/or snare portion 130. A visual or audible indicator (not shown) may be operably coupled to handle portion 120, snare portion 130 and/or sensor 125 to provide visual, audible or tactile feed back to the user to assure that the clamping pressure is within the desired range prior to activation of the instrument.

Alternatively, handle portion 120 may incorporate a spring mechanism 125a configured to prevent excessive force being applied to snare portion 130, thereby preventing overcompression of the tissue between first and second electrodes 134, 136. Spring mechanism 125a may include a compression spring (not shown) that deforms once the force applied to handle 126 exceeds the force necessary to accomplish effective sealing between first and second electrodes 134, 136. In an alternative embodiment, snare portion 130 may instead be advanced and retracted through the rotation of handle 126. In this manner, handle portion 120 may include a torque mechanism, e.g., torque wrench or the like, (not shown) which is precisely set to measure the torque (rotational force) applied to snare portion 130 so the closure pressure between electrodes 134, 136 will fall within the desired pressure range.

Figure 9:
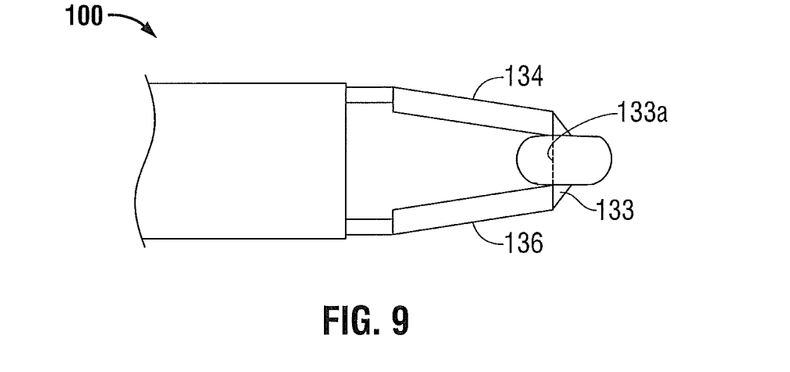
FIG. 9 is a partial top plan view of the distal end of the polyp removal device of FIGS. 6-8, as the stalk of the polyp is being severed.

Once the tissue of stalk "S" is sealed, handle 126 is partially advanced to extend a length of snare portion 130 from tubular member 110, thereby approximating proximal ends 134a, 136a of first and second electrodes, respectively, away from each other and exposing sealed stalk "S" to first sharpened surface 133a of connection member 133. While maintaining snare portion 130 relative to tubular member 110, tubular member 110 is retracted relative to polyp "P", thereby causing the engagement of stalk "S" with first sharpened surface 133a of connection member 133. Continued retraction of tubular member 110 causes the complete severing of stalk "S" (see FIG. 9).

When using polyp removal device 110, the likelihood of excessive bleeding is greatly reduced because the tissue is completely sealed prior to being cut. Using polyp removal device 110 further reduces the likelihood of creating an open wound that is susceptible to infection. In addition, the utilization of bipolar energy to seal a polyp or other tissue is safer than monopolar, e.g., because of less thermal and energy spread, thereby reducing the likelihood of perforations.

Figure 10:
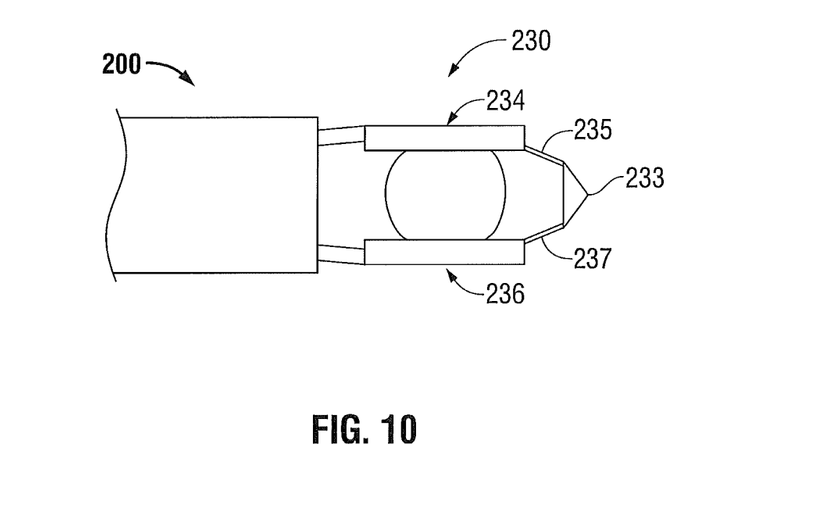
FIG. 10 is a partial top plan view of another illustrative embodiment of a polyp removal device of the present disclosure, in a retracted position about a polyp.

With reference now to FIG. 10, an alternative embodiment of the present disclosure is shown generally as polyp removal device 200. Polyp removal device 200 is substantially similar to polyp removal device 100 and will, therefore, only be described as relates to the differences therebetween. Snare portion 230 includes first and second electrodes 234, 236 and a connection member 233. Extending between first and second electrodes 234, 236 and connection member 233 are extension members 235, 237, respectively. Extension member 235, 237 permit first and second electrodes 234, 236 to be spaced further apart from one another in a second or sealing condition. In this manner, polyp removal device 200 may be used to excise larger polyps having a larger stalk.

Various changes in form, detail and operation of the polyp removal devices of the present disclosure may be made without departing from the spirit and scope of the present disclosure.

What is claimed is:

1. A tissue removal system comprising:
a tubular member having proximal and distal ends, the distal end including a spacer member that defines a plurality of apertures therethrough;
a connector shaft supported within the tubular member and having proximal and distal ends; and
a snare portion having first and second ends monolithically formed with the distal end of the connector shaft, the snare portion operably extending through the plurality of apertures of the spacer member and from the distal end of the tubular member, the snare portion movable relative to the spacer member and including a cutting member having a sharpened surface.

2. The tissue removal system of claim 1, further comprising a handle portion secured to the proximal end of the connector shaft and operatively coupled to the proximal end of the tubular member.

3. The tissue removal system of claim 2, wherein the handle portion is configured for operable engagement by a user and movable relative to the tubular member.

4. The tissue removal system of claim 2, wherein the sharpened surface of the cutting member is configured to cut tissue in response to movement of the handle portion in a proximal direction relative to the tubular member.

5. The tissue removal system of claim 1, wherein the snare portion is configured to grasp a stalk of a polyp.

6. The tissue removal system of claim 1, wherein the snare portion is configured to be retracted within the tubular member in response to movement of the connector shaft in a proximal direction.

7. The tissue removal system of claim 1, further including an electrosurgical generator.

8. The tissue removal system of claim 7, wherein the snare portion is electrically coupled to the electrosurgical generator.

9. The tissue removal system of claim 1, wherein first and second apertures of the plurality of apertures of the spacer member are spaced from one another to prevent a first portion of the snare portion from contacting a second portion of the snare portion.

10. The tissue removal system of claim 1, wherein the tubular member is configured for endoscopic insertion, laparoscopic insertion or transluminal insertion.

11. The tissue removal system of claim 2, wherein the handle portion includes handle configurations selected from the group consisting of pistol grip style handles, mechanically-actuated handles and remotely-actuated handles.

12. A tissue removal system comprising:
a tissue removal device comprising:
a tubular member having proximal and distal ends, the distal end including a spacer member that defines a plurality of apertures therethrough;
a handle portion operatively extending from the proximal end of the tubular member;
a connector shaft having a proximal end secured to the handle portion and a distal end;
a snare portion having first and second ends monolithically formed with the distal end of the connector shaft, the snare portion slidably supported within the tubular member, the snare portion movable through the plurality of apertures of the spacer member and from the distal end of the tubular member; and
a cutting member having a sharpened surface positioned on the snare portion; and
a generator configured to generate and deliver energy to the tissue removal device.

13. The tissue removal system of claim 12, wherein the energy is selected from the group consisting of radiofrequency energy, ultrasonic energy, microwave energy, and laser energy.

14. A method of removing a tissue mass of a body comprising:
providing a tissue removal device including a snare portion and a cutting member having a sharpened surface positioned on the snare portion, the snare portion including first and second ends monolithically formed with a distal end of a connector shaft;
moving the snare portion through a plurality of apertures defined through a spacer member to surround the tissue mass;
retracting the snare portion to capture the tissue mass within the snare portion;
delivering energy to the snare portion;
discontinuing delivery of energy to the snare portion; and
further retracting the snare portion such that the sharpened surface of the cutting member severs the tissue mass from the body.

15. The method of claim 14, wherein delivering energy to the snare portion further includes sealing the tissue mass.

16. The method of claim 15, further comprising:
monitoring electrical properties of the tissue mass during energy delivery;
detecting a predetermined condition; and
signaling that the tissue mass is ready to be severed.

17. The method of claim 14, further including preventing contact between a first portion of the snare portion and a second portion of the snare portion with the spacer member.

18. The tissue removal system of claim 1, wherein the snare portion includes at least one electrode that is hingedly connected to the cutting member.

19. The tissue removal system of claim 12, wherein the snare portion includes a proximal portion and a distal portion, the first and second ends of the snare portion are monolithically formed with the distal end of the connector shaft at the proximal portion of the snare portion.

20. The tissue removal system of claim 19, wherein a length of the snare portion extends from the proximal portion to the distal portion, the length of the snare portion remaining substantially constant as the snare portion moves between fully approximated and fully unapproximated positions to sever a tissue mass enclosed by the snare portion.

21. The tissue removal system of claim 1, wherein the spacer member is fixedly secured to the distal end of the tubular member.

\* \* \* \* \*